US009522260B2

(12) United States Patent
Mutus et al.

(10) Patent No.: US 9,522,260 B2
(45) Date of Patent: Dec. 20, 2016

(54) APPARATUS FOR THE CONTROLLED RELEASE OF TOPICAL NITRIC OXIDE

(75) Inventors: Bulent Mutus, Windsor (CA); Arthur Jarosz, Windsor (CA); Adam Faccenda, Amherstburg (CA); Xueji Zhang, Sarasota, FL (US)

(73) Assignee: University of Windsor, Windsor, Ontario (CA)

( * ) Notice: Subject to any disclaimer, the term of this patent is extended or adjusted under 35 U.S.C. 154(b) by 302 days.

(21) Appl. No.: 14/000,868

(22) PCT Filed: Feb. 22, 2012

(86) PCT No.: PCT/CA2012/000157
§ 371 (c)(1),
(2), (4) Date: Apr. 3, 2014

(87) PCT Pub. No.: WO2012/113060
PCT Pub. Date: Aug. 30, 2012

(65) Prior Publication Data
US 2014/0296773 A1    Oct. 2, 2014

Related U.S. Application Data

(60) Provisional application No. 61/457,318, filed on Feb. 25, 2011.

(51) Int. Cl.
| | | |
|---|---|---|
| A61M 35/00 | (2006.01) | |
| A61K 33/00 | (2006.01) | |
| A61L 15/44 | (2006.01) | |
| A61K 9/70 | (2006.01) | |
| A61K 31/095 | (2006.01) | |
| A61K 31/43 | (2006.01) | |
| A61K 38/06 | (2006.01) | |
| A61F 13/00 | (2006.01) | |

(52) U.S. Cl.
CPC ............ *A61M 35/00* (2013.01); *A61K 9/7084* (2013.01); *A61K 31/095* (2013.01); *A61K 31/43* (2013.01); *A61K 33/00* (2013.01); *A61K 38/063* (2013.01); *A61L 15/44* (2013.01); *A61F 2013/00646* (2013.01); *A61L 2300/114* (2013.01)

(58) Field of Classification Search
CPC .... A61M 35/00; A61K 38/063; A61K 31/095; A61K 9/7084; A61F 2013/00646; A61L 2300/114
See application file for complete search history.

(56) References Cited

FOREIGN PATENT DOCUMENTS

| | | |
|---|---|---|
| WO | WO 2006/100155 A1 | 9/2006 |
| WO | WO 2008/116497 A1 | 10/2008 |
| WO | WO 2009/049208 A1 | 4/2009 |

(Continued)

OTHER PUBLICATIONS

PCT International Search Report for PCT Counterpart Application No. PCT/CA2012/000157, 4 pgs., (May 17, 2012).

(Continued)

*Primary Examiner* — Bradley Osinski
(74) *Attorney, Agent, or Firm* — Blakely, Sokoloff, Taylor & Zafman LLP (57) ABSTRACT

A stable delivery system for the therapeutic release and application of nitric oxide to a patient suffering from a cutaneous injury or wound includes a S-nitrosothiol and transition element nanoparticles. The transition metal nanoparticles are selected to react with the S-nitrosothiol to release and diffuse nitric oxide into the injury or wound.

19 Claims, 7 Drawing Sheets

(56) References Cited

FOREIGN PATENT DOCUMENTS

| WO | WO 2010/048724 A1 | 5/2010 |
|----|-------------------|--------|
| WO | WO 2010/086637 A1 | 8/2010 |
| WO | WO 2012/052561 A2 | 4/2012 |

OTHER PUBLICATIONS

European Patent Office Communication enclosing Extended European Search Report for corresponding European Patent Application No. 12748979.7, 5 pages, (Feb. 24, 2015).
PCT Written Opinion of the International Searching Authority for PCT Counterpart Application No. PCT/CA2012/000157, 7 pages, (May 17, 2012).
PCT Notification Concerning Transmittal of International Preliminary Report on Patentability (Chapter I of the Patent Cooperation Treaty) for PCT Counterpart Application No. PCT/CA2012/000157, 9 pages, (Sep. 6, 2013).

APPARATUS FOR THE CONTROLLED RELEASE OF TOPICAL NITRIC OXIDE

CROSS-REFERENCE TO RELATED APPLICATIONS

This patent application is a U.S. National Phase Application under 35 U.S.C. 371 of International Application No. PCT/CA2012/000157, filed Feb. 22, 2012, entitled APPARATUS FOR THE CONTROLLED RELEASE OF TOPICAL NITRIC OXIDE, which claims the benefit of 35 USC §119(e) to U.S. Provisional Application Ser. No. 61/457,318, filed Feb. 25, 2011.

SCOPE OF THE INVENTION

The present invention relates to an apparatus for the controlled release of nitric oxide, and more preferably a portable apparatus adapted to provide for the topical release of a therapeutically beneficial amount nitric oxide (NO) in the treatment of cutaneous injuries.

BACKGROUND OF THE INVENTION

The use of nitric oxide (NO) as an inhalant for the vasodilation of pulmonary arterioles and improved blood flow to the lungs is well known. NO is known to diffuse from alveolar gas into the pulmonary vasculature of ventilated lung regions and cause relaxation of pulmonary vascular smooth muscles. Inhaled nitric oxide therapies advantageously prolong the time available for treating diseases or underlying symptoms such as hypertension or hypoxia.

More recently, the topical application of the nitric oxide as a therapy for cutaneous injuries has been proposed. Such treatments have however, proven problematical as to date the delivery and controlled release of topical NO to cutaneous wounds has proven problematic.

SUMMARY OF THE INVENTION

Accordingly, the present invention seeks to provide a stable delivery system or platform for the therapeutic release and application of nitric oxide to a patient, and more preferably to a patient suffering from a cutaneous injury or wound.

Another object of the invention is to provide a portable system for the stable storage and topical delivery of NO for use in the treatment of cutaneous wounds, and more preferably, cutaneous wounds which, for example, are obtained by reason of war or insurrection.

To at least achieve some of the foregoing objects, the inventors have appreciated an improved storage and delivery platform which is adapted for use in treatment systems used to treat cutaneous wounds by the controlled release and application of a topical nitric oxide thereto. The present invention further provides for the release and treatment of cutaneous injuries by the topical application of gaseous nitric oxide in concentrations selected to provide a therapeutic, antibacterial and/or enhanced wound healing properties.

More preferably, the storage and delivery system provides a NO delivery platform which is flexible in design to allow for the delivery of large boluses of nitric oxide for use in the acute treatment of wounds or which may be configured to allow for a slow or controlled release of a topical nitric oxide for chronic or sustained release for example, to modulate inflammation, angiogenesis and/or facilitate synthesized collagen to accelerate wound closure.

The present invention provides a number of different delivery platforms for use in or in conjunction with a variety of treatment systems including without limitations, creams and ointments, as well as bandages or dressings, and which achieve the release of NO by the mixture of binary components. In a most preferred embodiment, the binary components include S-nitrosothiol and one or more transition metal composites, and more preferably, gold, silver and/or copper-based nanoparticle composites. The delivery system storage and release platform contain such compounds or compositions in amounts selected to release therapeutic levels of exogenous NO when mixed, and furthermore may be provided with tunable kinetics to provide for either acute or chronic NO-release.

The delivery platform furthermore maybe incorporated into the treatment systems to provide for portability, thermal stability and/or suitable shelf life at room temperature and/or enhanced refrigerator storage life.

Accordingly, in one aspect, the present invention resides in a cutaneous injury treatment system comprising: a storage reservoir containing a volume S-nitrosothiol; a reactive medium comprising a transition metal component reactable with said S-nitrosothiol to release a therapeutically effective amount of nitric oxide, a storage barrier for maintaining said volume of S-nitrosothiol in said reservoir physically separate from said reactive medium during storage or transport of said cutaneous injury treatment system; and wherein said system is selectively activatable to effect the mixture of at least part of said volume of S-nitrosothiol and said reactive medium to release said amount of nitric oxide.

In another aspect, the present invention reside in a system for the topical delivery of nitric oxide to an injury comprising, a nitric oxide delivery platform comprising: a SNOG storage reservoir comprising a volume of a solution comprising SNOG solution; a reactive medium chamber housing a reactive transition metal complex reactive with said solution to release a therapeutically beneficial amount of nitric oxide gas; a mechano-disruptable membrane separating said reservoir from said transition metal complex, the mechano-disruptable membrane selected to rupture on the application of a predetermined force thereto to effect mixing of the solution with the transition metal complex and release nitric oxide gas.

In yet a further aspect, the present invention reside in a wound dressing system for the topical delivery of nitric oxide to a cutaneous injury comprising: a S-nitrosothiol storage reservoir comprising a S-nitrosothiol solution; a reactive medium chamber comprising at least one of transition metal composite selected from the group consisting of a gold-based nanoparticle composite, a silver-based nanoparticle composite, and a copper-based nanoparticle composition, the transition metal composites being reactive with said volume of S-nitrosothiol to release a therapeutically beneficial amount of nitric oxide; at least one of the storage reservoir and reactive medium chamber including a gas-permeable containment layer selected to allow for the movement of nitric oxide therethrough while substantially preventing movement of said S-nitrosothiol solution and/or said transition metal composite therepast; a mechano-disruptable membrane separating said storage reservoir from said reactive medium chamber, the mechano-disruptable membrane selected to rupture on the application of a predetermined force thereto to effect mixing of the S-nitrosothiol solution with the transition metal composite and a metal composite, and release nitric oxide gas through said gas-permeable containment layer.

BRIEF DESCRIPTION OF THE DRAWINGS

Reference may be had to the following description, taken together with the accompanying drawings in which.

DETAILED DESCRIPTION OF THE PREFERRED EMBODIMENTS

Figure 1A:
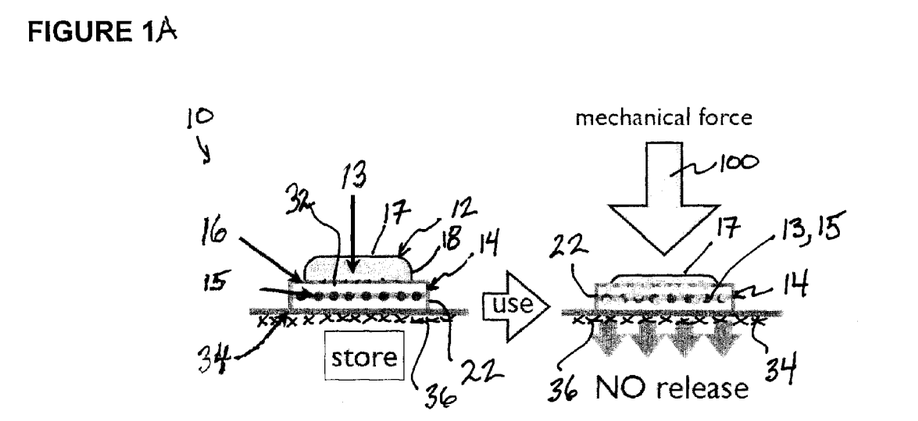
FIGS. 1A and 1B illustrate schematically a cutaneous injury treatment system for the release of NO in accordance with preferred embodiments of the invention.
Figure 1B:
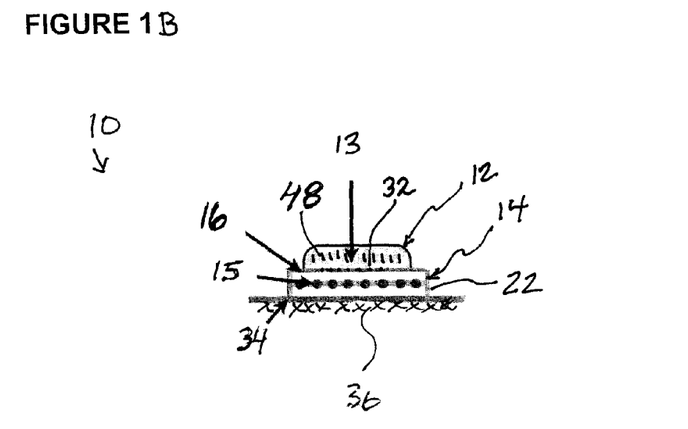
Figure 2:
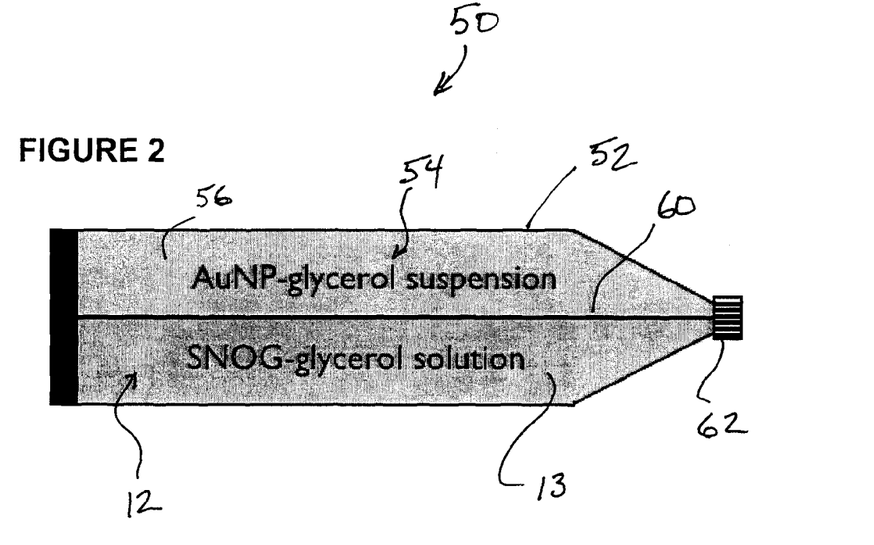
FIG. 2 illustrates schematically a cutaneous injury treatment system for the release of NO in accordance with a further embodiment of the invention.

Reference may be had to FIGS. 1A, 1B and 2 which illustrate cutaneous injury treatment systems 10, 50 which incorporates storage and delivery platform for the controlled release and delivery of topical nitric oxide to a cutaneous wound, in accordance with preferred embodiments. As will be described, in each treatment systems 10, 50, the storage and delivery platforms are provided for the controlled release of NO, whereby one or more transition metal composites, and preferably composites of group II transition metal nanoparticles such as gold, copper and/or silver nanoparticles, react stoichiometrically with S-nitrosothiols to yield NO, plus gold, copper and/or silver thiolates, as for example in the case of gold nanoparticles of (AuNP) by the following equation [Eq. 1]:

$$AuNP+RS\!-\!N\!=\!O \rightarrow N\!=\!O.+RS\!-\!AuNP \qquad [Eq.\ 1]$$

In a preferred treatment system 10 shown in FIG. 1A, a simplified bandage-type NO-release delivery platform is provided. The treatment system 10 includes a source storage reservoir 12 storing a volume of a nitric oxide donor solution 13, a reactive medium chamber 14 for storing a transition metal component 15 chosen to react with the donor solution 13 to release a therapeutically beneficial amount of nitric oxide on mixture therewith, and a barrier membrane 16 for maintaining the donor solution 13 in the storage reservoir 12 physically separated from the transition metal component in the chamber 14 during storage and/or transport of the treatment system 10. As will be described, the barrier membrane 16 is provided with a frangible or mechano-disruptable central portion 32 which is selected to tear or otherwise rupture upon the application of a predetermined threshold force thereto in use of the treatment system 10. In a simplified construction, the storage reservoir 12 includes fluid impervious top wall 17 and peripheral sidewall 18. The sidewall 18 is further sealed across its bottom edge by the mechano-disruptable portion 32 of the barrier membrane 16.

The reactive medium chamber 14 includes a substantially fluid impervious peripheral sidewall 22 which is initially sealed along its upper edge by the mechanical mechano-disruptable portion 32 of the barrier membrane 16. The lower edge of the sidewall 22 is sealed to a gas permeable membrane 34 which defines a lower extent of the reactive medium chamber 14. The gas permeable membrane 34 is chosen to permit the desired flow rate of nitric oxide therethrough, whilst preventing any movement of reacted or unreacted nitric oxide donor solution 13 or the transition metal component 15 therepast.

It is to be appreciated that in the use of the treatment system 10 of FIG. 1A, the gas permeable membrane 34 is to be positioned adjacent to a cutaneous wound or injury to be treated. In a most preferred construction, the treatment system 10 is provided as a delivery platform in the form of a bandage or dressing for the treatment of cutaneous injuries, and which could include without restriction include burns, cuts and/or puncture wounds. In this regard, the contacting surface of the gas permeable membrane 34 may be sterile and adapted for placement directly against or over the injury.

Although not essential the treatment system 10 could furthermore be provided with an outer dressing or gauze layer 36 covering the membrane 34, and which may or may not be impregnated with one or more of an antibacterial agent; an antibiotic agent, and/or anesthetic agents. It is to be appreciated, however, that the dressing or gauze layer 36 is chosen so as to not adversely effect or otherwise interfere with the transmission of nitric oxide gas therethrough.

Most preferably, the transition metal component 15 stored in the reactive medium chamber 14 incorporates up to four different transition metal nanocomposites. The final selection of the transition metal nanocomposites advantageously allows for tuning of SNOG-dentirosylatation kinetics and adjustment of the total and/or rate of NO yield.

Most preferably, AuNP-nanocomposites are employed in the delivery platform used in treatment system 10 of FIG. 1A. In a preferred application, a cotton gauze-substrate 40 (FIG. 4) impregnated AuNP (CG-AuNP) is sealed within the chamber 14 as the reactive transition metal component 15. In alternate embodiments, however, polydimethylsiloxane-AuNP nanocomposites (PDMS-AuNP); Glass-AuNP nanocomposites (G-AuNP); and/or Sephadex®-AuNP complexes (Sx-AuNP) also may preferably be used either in substitution or combination.

In the initial assembly of the treatment system 10, a selected volume of a liquid S-nitrosothiol solution 13 is introduced into the reservoir 12 by injection through the top wall 17. It is to be appreciated that other modes of manufacture will however, be apparent. The S-nitrosothiol solution is chosen for the stable storage and/or carriage of a therapeutically beneficial amount of nitric oxide and may by way of non-limiting example, comprise S-nitroso-N-acetyl-D-penicillamine (SNAP), or more preferably S-nitrosoglutathione (SNOG).

In the embodiment of the treatment system 10 shown in FIG. 1A, during storage and transport of the delivery platform the volume of S-nitrosoglutathione (SNOG) solution 13 is housed within SNOG-storage reservoir 12. Up to the time of use, SNOG is physically separated from the AuNP-nanocomposite gauze 40 by the solution 13 or mechano-disruptable membrane 32. As a result, during storage, the SNOG solution 13 and the AuNP nanocomposite reactant gauze 40 are prevented from mixing by the membrane 32, and no NO is released.

When use of the treatment system 10 is required, the membrane 32 separating SNOG solution and the AuNP-nanocomposite gauze 40 is ruptured by applying a small predetermined threshold downward pressure (arrow 100) on the top wall 17 of SNOG-storage reservoir 12. The rupture of the membrane 32 allows the SNOG solution to move into the reactive medium chamber 14 and mix with the AuNP gauze 40 causing the release of NO [Eq. 1]. The released NO diffuses outwardly from the reactive medium chamber 14 into the patient's wound or damaged skin through the gas-permeable membrane 34 and dressing layer 36.

The applicant has appreciated that by varying the concentrations of the reactive ingredients in both the SNOG and/or the reactive medium transition metals, the overall concentration and/or volume of released nitric oxide may be easily controlled. In addition, by varying the specific properties of the selectively gas permeable membrane 34, the release rate of nitric oxide can be regulated. By way of example, it is possible to vary NO release from a slow stage release (NMOL/HR) to a very fast release (i.e. in the range of micromole/HR) by controlling one or more of the gas permeable membrane 34 composition and/or thickness. The gas permeable membrane 34 preferably both controls the rate of delivery of NO and is impermeable to water, thus both controlling NO delivery whilst keeping the reactive ingredients separated from the patient's wound.

FIG. 1B illustrates a modified bandage-type cutaneous injury treatment system 10 having substantially the same construction as that of FIG. 1A, wherein like reference numerals are used to identify like components. In FIG. 1B a set of plastic pins 48 or other suitable mechanical features are further embedded or otherwise provided with the S-nitrosothiol storage reservoir 12. The pins 48 most preferably align and point towards the mechano-disruptable membrane 32. When the force 100 is applied to, the top wall 17 of the reservoir 12, the mechanical engagement of the pins 48 facilitate both a breakage of the membrane 32 as well as the mixture of the S-nitrosothiol solution with the AuNP nanocomposite gauze 40.

FIG. 2 shows a binary cream-type storage and delivery platform whereby a cutaneous injury treatment system 50 in the form of a squeezable tube is provided in accordance with another embodiment of the invention, and in which like reference numerals are used to identify like components. In FIG. 2, the treatment system 50 is provided as a two-part squeezable tube 52. The interior of the tube 52 is divided into physically separated reservoirs including a nitric oxide donor composition/compound reservoir 12 and a reservoir 54 for a liquid transition metal component. In a most preferred embodiment, the reservoir 54 houses a volume 56 of transition metal nanoparticle suspension such as AuNP-glycerol suspension 56, with the reservoir 12 housing a selected volume 13 of a SNOG glycerol solution.

Within the tube 52, the AuNP-glycerol suspension 56 is separated from the SNOG-glycerol solution 58 by a fluid impervious membrane 60. The membrane 60 bisects the squeezable tube 52 (FIG. 2) to an open end sealed with a removable cap 62.

The delivery platform of the treatment system 50 of FIG. 2 is selected to allow for the release and co-mixture of the SNOG-glycerol solution 13 and the AuNP-glycerol suspension 56 in the form of a viscous or semi-viscous cream or gel. It is to be appreciated, however, that in another embodiment, the tube 52 could equally store and release more or less viscous solutions of other S-nitrosothiols and/or other transition element nanoparticle suspensions.

When the cream is dispensed from the tube 52 and initially mixed as it is administered on a patient's skin, NO is released. A useful range of NO generation can be obtained by varying the AuNP: SNOG ratios. In this configuration, the patient's skin comes in contact with both SNOG and AuNP. Therefore the bacteriostatic and wound healing ability of the individual components and the mixture can be adjusted.

The applicant has appreciated that the platforms of the treatment systems 10, 50 shown in FIGS. 1A, 1B and 2 advantageously allow for tailored control for the delivery of NO to treat a variety of cutaneous injuries, including those which could occur by act of insurrection or war on a battlefield, and which may advantageously provide by broad spectrum coetaneous antimicrobial activity and enhanced wound healing in vivo.

Figure 3:
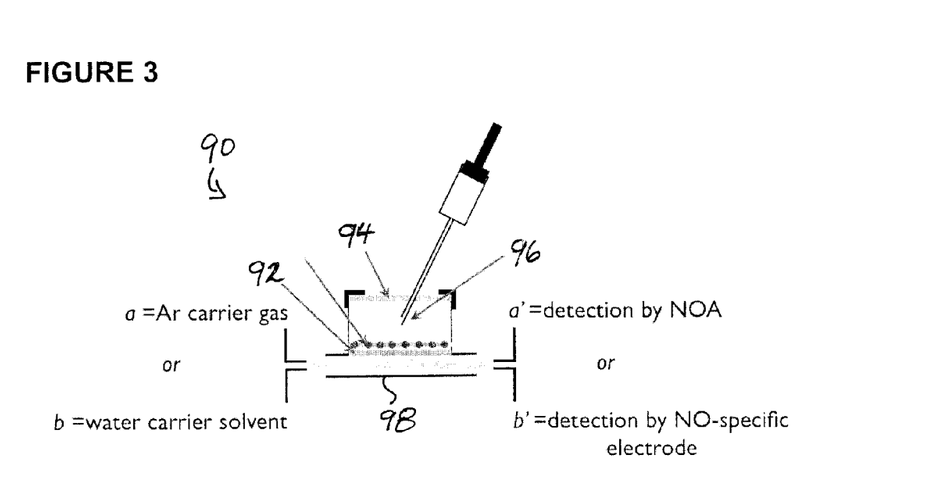
FIG. 3 illustrates schematically a testing line used in the verification of the NO treatment systems shown in FIGS. 1A and 2.

Clinical Studies—1. Test Apparatus for Prototype Characterizing NO-Release Rates and Yield in the Proposed Platforms:

The feasibility of the proposed delivery platforms contemplated by the treatment systems 10, 50 as a NO-releasing bandages and cream respectively, was tested in the apparatus 90 shown in FIG. 3. The apparatus 90 was chosen to primarily mimic the design of the bandage-type treatment system 10 (FIG. 1A). In testing, an AuNP-nanocomposite was placed on top of a gas-permeable (porous polycarbonate) membrane 92 and sealed with a gas-tight septum 94 through which SNOG was introduced with a syringe 96, simulating the mixing of the binary components upon breaking of the mechano-disruptable membrane 32 (FIG. 1A). With the test apparatus 90, the released NO escaping the gas-permeable membrane 92 was directly quantified by sampling an Ar(g) stream 98 in a chemiluminescent NO-analyzer. Alternatively, water can be passed over the gas-permeable membrane and the dissolved-NO can be determined with a suitable NO-specific electrode.

2. Testing NO Release Rates and NO-Yield of the Various AuNP-Nanocomposites

In preliminary testing using the apparatus 90 of FIG. 3, preferred gold nanoparticle composites were tested as follows:
  i) cotton gauze substrate impregnated with gold nanoparticles (CG-AuNP);
  ii) Polydimethylsiloxane gold nanoparticle nanocomposites (PDMS-AuNP);
  iii) Glass gold nanoparticle nanocomposites (G-AuNP); and
  iv) cross-linked dextran gel (i.e. Sephadex®) gold nanoparticles complexes (Sx-AuNP).

The AuNP-nanocomposites i) to iv) were placed in the apparatus 90 and exposed to increasing amounts of SNOG. The rate of NO release is determined from the initial rates of the slope of [NO] vs. time data (at 37° C.). The NO-yield was determined from the area under the curve (AUC) from the [NO] vs. time data in the presence of saturating amounts of SNOG.

The setup in FIG. 3 also enabled the determination of the NO-release characteristics of delivery platform 50 (FIG. 2). In this case, the AuNP-nanocomposite layer was removed from the apparatus. An AuNP-glycerol suspension and the SNOG solution in glycerol were introduced via two different syringes, thus simulating the mixing of the binary gels (FIG. 2).

Testing dates shows that PDMS-AuNP nanocomposites are ideally suited for slow, low concentration release of NO. This is because only one face of the PDMS-AuNP will contain the AuNP. In test, these were placed in the apparatus 90 (FIG. 3) with the AuNP-rich face pointing at the gas-tight septum 94. This corresponds to the AuNP-rich face pointing at the mechano-disruptable membrane 32 in the embodiment NO-releasing bandage-type dressings of systems 10, 50 of FIGS. 1A and 1B*. Upon coming in contact with the SNOG solution, NO is produced and diffuses through the PDMS membrane. As PDMS is permeable to gases like $O_2$, $CO_2$ and $N_2$, is therefore expected to also be permeable to NO. Furthermore, the rate of NO-diffusion is proportional to the thickness of the PDMS-AuNP membrane. Therefore correlation of the rate of NO release to the PDMS thickness as well as the surface AuNP-density can be regulated by controlling the $HAuC_4$ to citrate ratio.

3. Characterized Components Complete Platforms for Preferred Characteristics with Respect to Thermal Stability, Room Temperature Shelf Life, Refrigerated Storage Life.

All of the AuNP-nanocomposites i) to iv) as well as SNOG solutions 1 mM, dissolved in distilled deionized water and containing 100 µM diethylenetriaminepentaacetic acid (DPTA) a metal chelator were stored at 5° C., 25° C. and 55° C. for 1 month. These components were then added to the testing apparatus 90 (FIG. 3) and their NO-release characteristics were compared to fresh samples.

It has been discovered that AuNP reacts with S-nitrosothiols to release stoichiometric amounts of NO [Eq. 1]. In addition, a series of AuNP nanocomposites were prepared that can serve in the present application as sources of immobilized AuNP, that when exposed to S-nitrosothiols result in the stoichiometric release of NO.

Most preferred constructions include:

i) Cotton Gauze-Impregnated AuNP (CG-AuNP)

Figure 4:
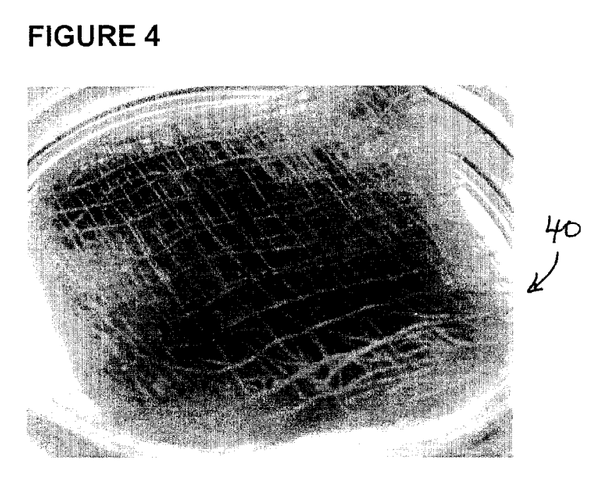
FIG. 4 provides a photograph illustrating an AuNP impregnated gauze for use in the treatment system of FIG. 1A.
Figure 5:
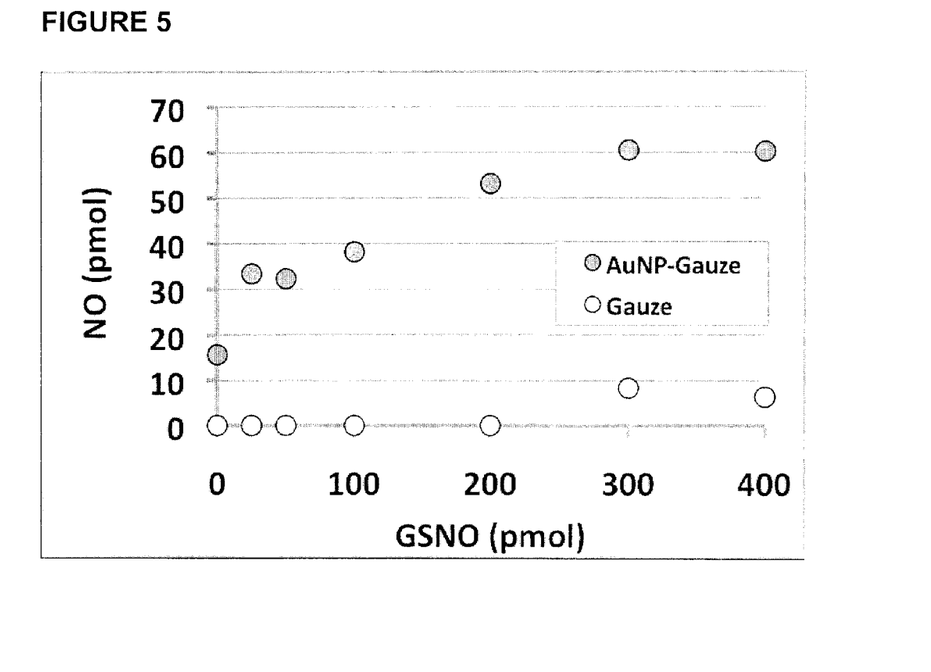
FIG. 5 illustrates graphically the denitrosylation of S-nitrosothiol by AuNP physisorbed on cotton gauze.

In one simplest and most cost effective manner to prepare an AuNP-nanocomposite, cotton gauze with AuNP (~10 nm) is prepared by a conventional citrate reduction method. Upon drying of the gauze (60° C. for 3 h) the AuNP are physisorbed to the cotton and do not leach out by soaking in water (FIG. 4). The CG-AuNP gauze 40 efficiently denitrosylates SNOG (FIG. 5). In addition S-nitrosothiol denitrosylation activity (i.e. NO release by [Eq. 1]) of dried CG-AuNP complex also does not decay for up to a month of storage at room temperature.

ii) Polydimethylsiloxane-AuNP Nanocomposites (PDMS-AuNP)

Figure 6:
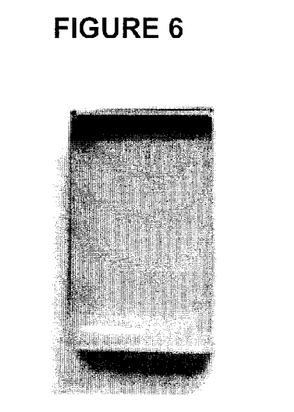
FIG. 6 illustrates the growth of AuNP on a polydimethylsiloxane polymer substrate.
Figure 7:
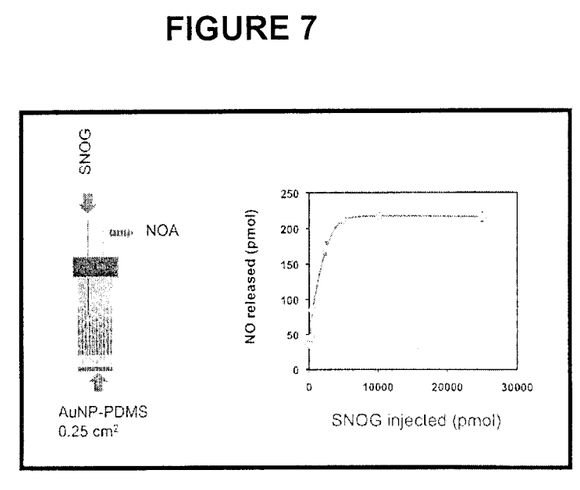
FIG. 7 illustrates graphically the ability of PDMS-AuNP nanocomposites to denitrosylate S-nitrosoglutathione (SNOG)

In an alternate procedure, AuNP are grown on the surface of polydimethylsiloxane(PDMS) polymers by layering a mixture of $HAuCl_3$ and citrate on polymerized PDMS (FIG. 6). The ability of PDMS-AuNP nanocomposites to denitrosate SNOG was tested by injecting increasing amounts of SNOG over ~0.25 cm² PDMS-AuNP formed in the bottom of septa-sealed vials. The amount of NO released was quantified with the aid of a chemiluminescent NO analyzer (NOA). The studies indicate that the PDMS-AuNP surface could release NO at rates of ~0.9 nmol $NO/cm^2$ (FIG. 7). The AuNP-density on the PDMS surface and by extension the NO-release yield can be regulated by varying the $HAuCl_4$:citrate ratio layered on the PDMS.

iii) Glass-AuNP Nanocomposites (G-AuNP)

Figure 8:
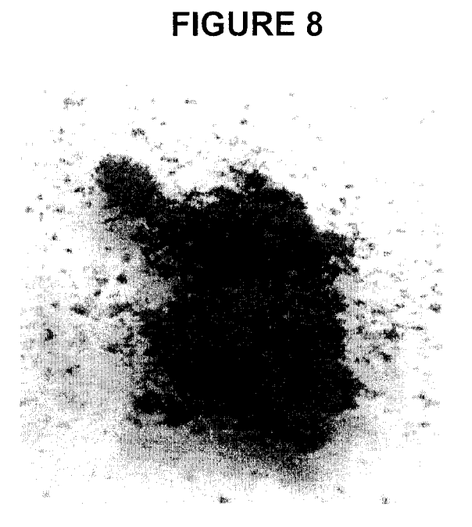
FIG. 8 illustrates pulverized G-AuNP powder for use in the NO storage and delivery platforms used in the injury treatment systems of FIGS. 1A and 1B.
Figure 9:
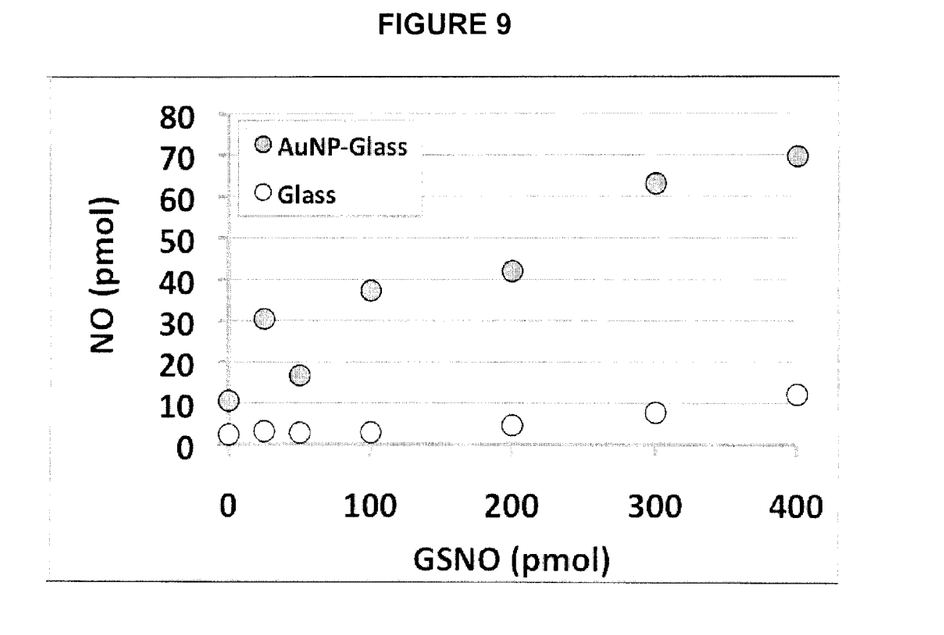
FIG. 9 shows graphically the release of NO by the mixture of G-AuNP powder and SNOG.

A sol-gel method was used to synthesize G-AuNP nanocomposites containing gold nanoparticles (AuNPs) ranging in size from 10 nm to 100 nm. The G-AuNPs were then pulverized into a powder (FIG. 8) and placed between the mechano-disruptable and gas permeable membranes of the type shown in FIG. 1A. These G-AuNPs are very efficient in releasing NO from SNOG (FIG. 9).

iv) Sephadex-AuNP Complexes (Sx-AuNP)

Figure 10:
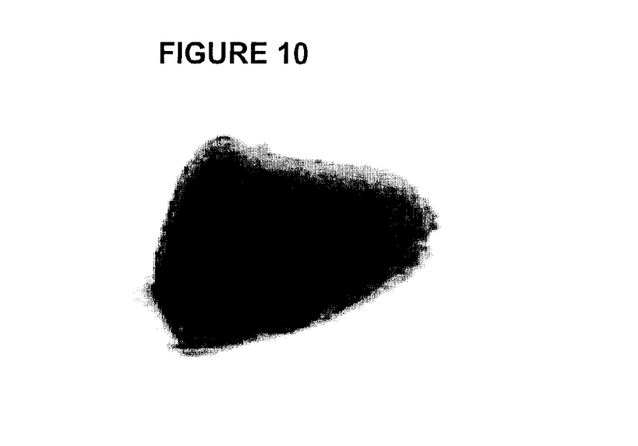
FIG. 10 is a photograph showing the physiosorption of AuNP to Sephadex®.
Figure 11:
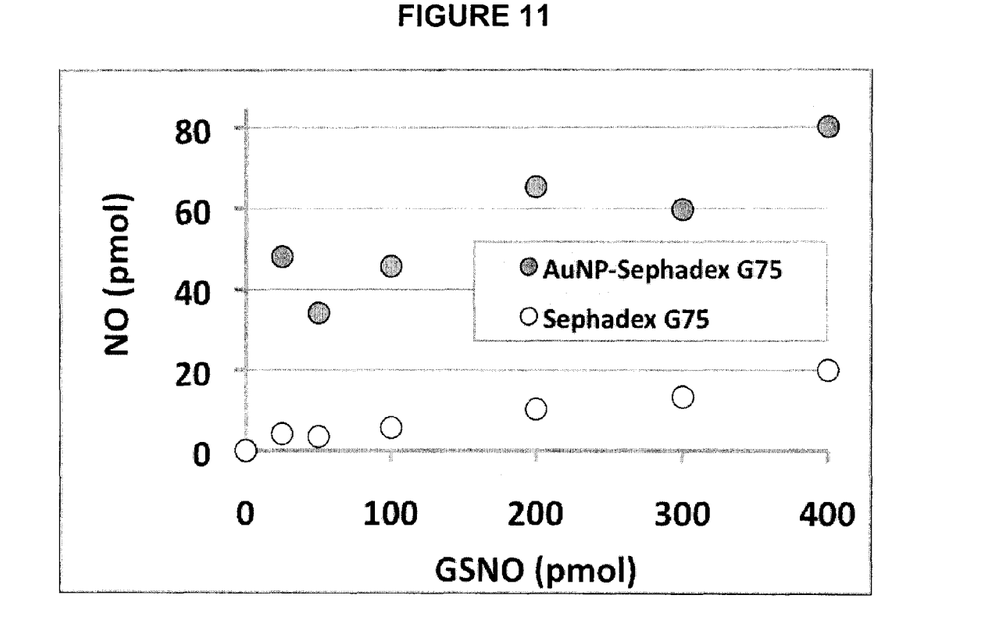
FIG. 11 illustrates graphically the release of NO from SNOG on mixture with Sephadex-gold nanoparticles.

In an alternate method, citrate capped AuNP can be included within cross-linked dextran (i.e. Sephadex®) gel beads (G-75 and larger exclusion volumes). Once included the AuNP appears to be physisorbed to the Sephadex as the AuNP will not elute from Sx-AuNP packed columns washed up to 1000-column volumes with aqueous buffers with high ionic strength buffers (1 M) or in the presence of denaturants like 6M urea (FIG. 10). The Sx-AuNP are as efficient as G-AuNP in releasing NO from SNOG (FIG. 11).

The aforementioned sample AuNP-nanocomposites may prove particularly suitable for use in the proposed delivery platform 10 shown in FIG. 1 as NO releasing agents in cutaneous wound bandages and dressings.

Preliminary studies have determined that the AuNP-composites i) to iv) are thermally stable for 7 days at 40° C. The bond dissociation energies of the S—NO bond in a variety of S-nitrosothiols indicate that thermal stability of SNOG and S-nitrosothiols are similar to those found for the O—O bonds of dialkyl peroxides (ca. 34-39 kcal/mol) which possess half-lives with respect to unimolecular O—O homolysis of years at temperatures of 25-40° C. The thermal unstability has therefore been shown to be related to metal contamination in the S-nitrosothiol solutions since the addition of metal chelators such as diethylenetriaminepentaacetic acid (DPTA) prevented the thermal decomposition S-nitrosothiols at 37° C. In preliminary experiments, solid SNOG was thermally stable to storage at 40° C. for one week. SNOG solutions (1 mM) containing DPTA (0.1 mm) decomposed ~5% upon incubation at 40° C. for 7 days. Stability of the SNOG may be increased further by either suspending it in polyethylene glycol or dissolving it in glycerol.

AuNP-nanocomposites advantageously have different rates of NO release as well a NO-yield, providing an array of flexible NO-release options useful in the various treatment modalities in battlefield environments.

The AuNP-PDMS nanocomposites are ideally tailored for slow NO-release suited chronic exposure to modulate inflammation, angiogenesis, and synthesize collagen to accelerate wound closure. The cream (i.e. treatment system 50) on the other hand may be used to yield rapid and large amounts of NO for bacteriostatic/wound cleaning applications.

In an alternate embodiment, it is envisioned that the invention of both delivery platforms of the treatment systems 10, 50 may be used in combination, as for example to provide both the initial rapid NO bacterialcidal properties, as well long termed sustained release.

Further, while the most preferred embodiment describes the use of gold nanoparticles as part of the nanocomposite mediums for reaction with S-nitrosothiols, the inventors have appreciated that in the present invention, other transition metal nanoparticles may also be used. These could therefore include silver nanoparticles and/or copper nanoparticles used either in substitution or in conjunction with AuNP, depending on the NO release rates and/or concentrations to be achieved.

While the detailed description describes and illustrates various preferred embodiments, the invention is not so limited. Modifications and variations will now appear to a person skilled in the art. For a definition of the invention, reference may be had to the appended claims.

We claim:

1. A cutaneous injury treatment system comprising:
a storage reservoir containing a volume of S-nitrosothiol;
a reactive medium comprising a transition metal component reactable with said S-nitrosothiol to release a therapeutically effective amount of nitric oxide, the reactive medium being selected from the group consisting of a polydimethylsiloxane nanocomposite, a glass nanocomposite impregnated with at least one of gold nanoparticles, silver nanoparticles and copper nanoparticles, and a cotton gauze substrate impregnated with at least one of gold nanoparticles, silver nanoparticles and copper nanoparticles,
a storage barrier for maintaining said volume of S-nitrosothiol in said reservoir physically separate from said reactive medium during storage or transport of said cutaneous injury treatment system; and
wherein said system is selectively activatable to effect the mixture of at least part of said volume of S-nitrosothiol and said reactive medium to release said amount of nitric oxide.

2. The system of claim 1, wherein said storage barrier comprises a mechano-disruptable membrane, whereby rupture of said mechano-disruptable membrane effects mixture of said at least part of said volume of S-nitrosothiol and said reactive medium.

3. The system of claim 2, wherein said reactive medium comprises said cotton gauze substrate, and wherein said cotton gauze substrate is impregnated with gold nanoparticles.

4. The system of claim 2, wherein the reactive medium comprises said polydimethylsiloxane nanocomposite.

5. The system of claim 2, wherein the reactive medium comprises said glass nanocomposite and wherein said glass nanocomposite is impregnated with gold nanoparticles.

6. The system of claim 1, wherein said S-nitrosothiol is selected from the group consisting of S-nitroso-N-acetyle-D-penicillamine (SNAP) and S-nitrosoglutathione (SNOG).

7. The system as claimed in claim 1 further comprising a gas-permeable containment layer selected to allow for the movement of nitric oxide therethrough, while substantially preventing the movement of said S-nitrosothiol or said reactive mixture therepast.

8. The system as claimed in claim 7 further comprising a gas-permeable dressing layer substantially adjacent to said gas-permeable containment layer for juxtaposed application to a cutaneous wound.

9. A system for the topical delivery of nitric oxide to an injury comprising,
a nitric oxide delivery platform comprising:
a S-nitrosoglutathione (SNOG) storage reservoir comprising a volume of a solution comprising SNOG solution;
a reactive medium chamber housing a reactive transition metal complex reactive with said solution to release a therapeutically beneficial amount of nitric oxide gas;
a mechano-disruptable membrane separating said reservoir from said transition metal complex, the mechano-disruptable membrane selected to rupture on the application of a predetermined force thereto to effect mixing of the solution with the transition metal complex and release nitric oxide gas, and
wherein the reactive transition metal complex is selected from the group consisting of cotton gauze substrate impregnated with at least one of gold nanoparticles, silver nanoparticles and copper nanoparticles, a polydimethylsiloxane nanocomposite comprising at least one of gold nanoparticles, silver nanoparticles and copper nanoparticles, and a glass nanocomposite impregnated with at least one of gold nanoparticles, silver nanoparticles and copper nanoparticles.

10. The system of claim 9, wherein the injury comprises a cutaneous wound, and wherein the reactive medium chamber includes a selectively permeable membrane, the selectively permeable membrane chosen to allow a diffusion of released nitric oxide therethrough to said injury in a substantially controlled release manner.

11. The system of claim 9, wherein the reactive transition metal complex comprises a cross-linked dextran gel complexed with at least one of gold nanoparticles, silver nanoparticles and copper nanoparticles.

12. The system as claimed in claim 9 further comprising a gas-permeable containment layer selected to allow for the movement of nitric oxide therethrough while substantially preventing the movement of said solution or said reactive transition metal therepast.

13. The system as claimed in claim 12 further comprising a gas-permeable dressing layer substantially adjacent to said gas-permeable containment layer for juxtaposed application to a cutaneous wound.

14. A wound dressing system for the topical delivery of nitric oxide to a cutaneous injury comprising:
a S-nitrosothiol storage reservoir comprising a S-nitrosothiol solution;
a reactive medium chamber comprising at least one of a transition metal composite selected from the group consisting of a cotton gauze substrate impregnated with at least one of gold nanoparticles, silver nanoparticles and copper nanoparticles, a polydimethylsiloxane nanocomposite, and a glass nanocomposite impregnated with at least one of gold nanoparticles, silver nanoparticles and copper nanoparticles, the transition metal composites being reactive with a volume of S-nitrosothiol to release a therapeutically beneficial amount of nitric oxide;
at least one of the storage reservoir and reactive medium chamber including a gas-permeable containment layer selected to allow for the movement of nitric oxide therethrough while substantially preventing movement of said S-nitrosothiol solution and/or said transition metal composite therepast;
a mechano-disruptable membrane separating said storage reservoir from said reactive medium chamber, the mechano-disruptable membrane selected to rupture on the application of a predetermined force thereto to effect mixing of the S-nitrosothiol solution with the transition metal composite and a metal composite, and release nitric oxide gas through said gas-permeable containment layer.

15. The system of claim 14, wherein the transition metal composite comprises said cotton gauze substrate, wherein said cotton gauze substrate is impregnated with gold nanoparticles.

16. The system of claim 14, wherein the transition metal composite comprises said polydimethylsiloxane nanocomposite, wherein said polydimethylsiloxane comprises gold nanoparticles.

17. The system of claim 14, wherein the transition metal composite comprises said glass nanocomposite, wherein said glass nanocomposite is impregnated with gold nanoparticles.

18. The system of claim 14, wherein said S-nitrosothiol comprises S-nitrosoglutathione (SNOG).

19. The system of claim 14, wherein said S-nitrosothiol comprises S-nitroso-N-acetyl-D-penicillamine (SNAP).

* * * * *